(12) United States Patent
Bouasaysy et al.

(10) Patent No.: US 11,565,079 B2
(45) Date of Patent: Jan. 31, 2023

(54) SUPPORT CATHETER (71) Applicant: ReFlow Medical, Inc., San Clemente, CA (US)

(72) Inventors: Outhit Bouasaysy, Corona, CA (US); Isa Rizk, San Diego, CA (US); John Fulkerson, Rancho Santa Margarita, CA (US)

(73) Assignee: REFLOW MEDICAL, INC., San Clemente, CA (US)

( * ) Notice: Subject to any disclaimer, the term of this patent is extended or adjusted under 35 U.S.C. 154(b) by 51 days.

(21) Appl. No.: 16/993,132

(22) Filed: Aug. 13, 2020

(65) Prior Publication Data
US 2021/0046279 A1 Feb. 18, 2021

Related U.S. Application Data (60) Provisional application No. 62/886,229, filed on Aug. 13, 2019.

(51) Int. Cl.
*A61M 25/00* (2006.01)
*A61M 25/01* (2006.01)

(52) U.S. Cl.
CPC ....... *A61M 25/005* (2013.01); *A61M 25/0012* (2013.01); *A61M 25/0108* (2013.01); *A61M 2025/0046* (2013.01)

(58) Field of Classification Search
CPC ............ A61M 25/005; A61M 25/0012; A61M 2025/0046; A61M 2025/0059; A61M 2025/0062; A61M 25/0045; A61M 2025/0047
See application file for complete search history.

(56) References Cited

U.S. PATENT DOCUMENTS

| | | | | |
|---|---|---|---|---|
| 4,806,182 A * | 2/1989 | Rydell | ................... | B29C 66/71 |
| | | | | 156/303.1 |
| 5,658,264 A * | 8/1997 | Samson | ............ | A61M 25/0053 |
| | | | | 604/526 |
| 5,951,539 A * | 9/1999 | Nita | ..................... | A61M 25/005 |
| | | | | 604/524 |
| 6,217,566 B1 * | 4/2001 | Ju | ..................... | A61M 25/0052 |
| | | | | 604/526 |

(Continued)

FOREIGN PATENT DOCUMENTS

| CN | 109803712 | 5/2019 |
|---|---|---|
| WO | WO 2006/031874 | 3/2006 |

(Continued)

OTHER PUBLICATIONS

International Search Report and Written Opinion from PCT/US2020/046219, dated Dec. 1, 2020, 7 pages.

*Primary Examiner* — Julian W Woo
(74) *Attorney, Agent, or Firm* — BakerHostetler (57) ABSTRACT

A delivery device can be provided with a low outer profile and high flexibility for navigating tortuous anatomy. An inner lumen defined by a shaft of the delivery device provides adequate space for delivery devices to target anatomy. Additionally, the delivery device maintains the patency of its lumen even when positioned within tortuous anatomy. The turns of filar(s) forming a coil of the shaft adjust their axial spacing relative to each other to avoiding buckling that would otherwise result in a narrowing of the inner lumen.

18 Claims, 5 Drawing Sheets

(56) References Cited

U.S. PATENT DOCUMENTS

| | | | | |
|---|---|---|---|---|
| 7,914,466 | B2 * | 3/2011 | Davis | A61M 25/0054 |
| | | | | 600/585 |
| 8,231,551 | B2 * | 7/2012 | Griffin | A61M 25/0051 |
| | | | | 600/585 |
| 8,337,425 | B2 | 12/2012 | Olson | |
| 8,403,912 | B2 * | 3/2013 | McFerran | A61M 25/0041 |
| | | | | 604/525 |
| 8,591,495 | B2 * | 11/2013 | Fischell | A61M 25/0662 |
| | | | | 604/526 |
| 10,245,050 | B2 | 4/2019 | Kugler | |
| 11,096,703 | B2 * | 8/2021 | Panian | A61M 1/0023 |
| 2004/0002728 | A1 | 1/2004 | Speck et al. | |

FOREIGN PATENT DOCUMENTS

| | | |
|---|---|---|
| WO | WO 2015/119075 | 8/2015 |
| WO | WO 2018/185917 | 10/2018 |
| WO | WO 2018/221218 | 12/2018 |

\* cited by examiner

SUPPORT CATHETER

CROSS-REFERENCE TO RELATED APPLICATION

This application claims the benefit of U.S. Provisional Application No. 62/886,229, entitled "SUPPORT CATHETER," filed Aug. 13, 2019, the entirety of which is incorporated herein by reference.

TECHNICAL FIELD

The present description relates in general to operations within a body vessel and in particular to catheters and methods for delivering devices within a body vessel.

BACKGROUND OF THE DISCLOSURE

A variety of delivery devices can be used to deliver other interventional devices to a desired treatment location within a patient. Examples of such delivery devices include catheters that travel within body vessels and provide a lumen for travel by interventional devices to reach a target location for treatment. Catheters can travel intravascularly within blood vessels of a patient to facilitate treatment at the target locations therein. Interventional devices for use with such catheters can include guidewires, stents, implants, balloon devices, crossing devices, and the like.

The description provided in the background section should not be assumed to be prior art merely because it is mentioned in or associated with the background section. The background section may include information that describes one or more aspects of the subject technology.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

The present technology relates generally to systems, methods, and devices for treating conditions within a patient (e.g., vascular conditions within blood vessels). Specific details of several embodiments of the present technology are described herein with reference to FIGS. 1-9.

The devices described herein can be applied to treat a variety of conditions including, without limitation, (e.g., chronic total occlusions ("CTO"), full occlusions, partial occlusions, occlusions resulting from a thrombus, occlusions resulting from an embolism, occlusions resulting from atherosclerosis, etc.). Additionally, other embodiments of the present technology can have different configurations, components, or procedures than those described herein. For example, other embodiments can include additional elements and features beyond those described herein, or other embodiments may not include several of the elements and features shown and described herein.

Conventional support catheters are typically constructed with either polymer braided shafts or multi-filar wire shafts with a polymer jacket, radiopaque polymer tip, and a hub. As such a support catheter is placed over a guidewire and encounters increased tortuosity, the amount of sliding friction increases in the guidewire lumen. In some instances, complete binding occurs. To alleviate the sliding friction between the catheter shaft ID and guidewire, some devices include a lubricious liner on the inner diameter of other structures.

Embodiments of the present disclosure provide delivery devices with reduced sliding friction by including a lubricious coating in a configuration that also minimizes the contact surfaces of the catheter. This can be achieved by coating the individual wires of a helical winding arrangement instead of a conventional liner in the ID. The coated wires wind helically and move relative to each other as needed to reduce binding in tortuous anatomy.

Figure 1:
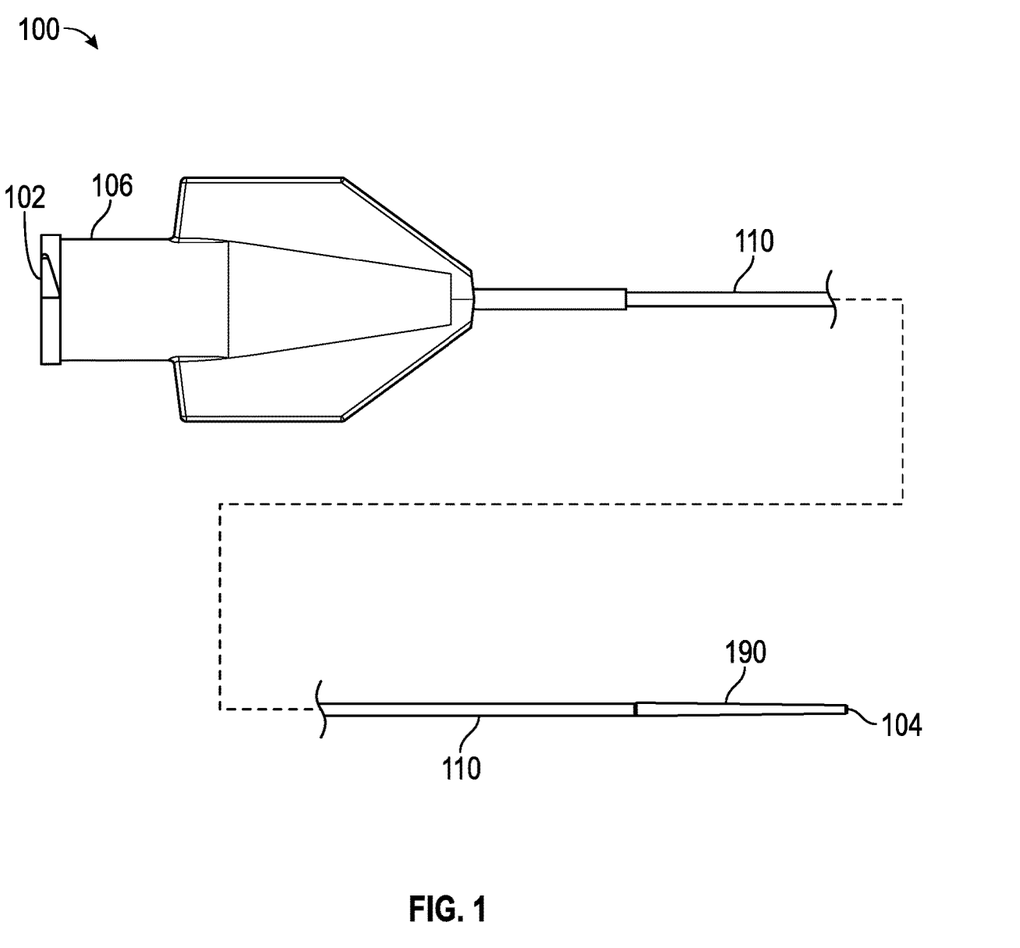
FIG. 1 illustrates a side view of a delivery device.

As shown in FIG. 1, a system can include a delivery device 100 for delivering another device through a lumen thereof. The delivery device 100 can include a connector 106 at and/or defining a proximal end portion 102 of the delivery device 100 and providing a handle, luer, connector, and/or hub. For example, the connector 106 can include a mating feature and/or a receiving feature for securely coupling to other components. The connector 106 can include a touhy bourst seal configured to secure a position of one or more devices within the delivery device 100.

The delivery device 100 can further include a distal tip 190 at and/or defining a distal end portion 104 of the delivery device 100. The distal tip 190 can include a radiopaque distal tip (e.g., polymer, tungsten, barium, etc.). The delivery device 100 can further include a shaft 110 extending between the connector 106 and the distal tip 190. The connector 106 can be configured to be positioned at a location external to a patient, and the shaft 110 can be configured to position the distal tip 190 (e.g., intravascularly) at or near a complete or partial occlusion within a blood vessel of the patient. The delivery device 100 can have a lumen extending from the connector 106 to the distal tip 190 and/or a side port 150. The delivery device 100 can receive one or more devices (e.g., guidewire) into the lumen through the distal tip 190. The delivery device 100 can receive one or more devices (e.g., interventional device, not shown) into the lumen through the connector 106. The delivery device 100 can include a strain relief element between the shaft 110 and another portion at the connector 106. For example, the strain relief element can surround or otherwise engage the shaft 110 at a proximal end thereof.

The shaft 110 can be sized and shaped for intravascularly accessing a target site (e.g., treatment site) of the patient. In some embodiments, for example, the shaft 110 has a length of about 150 cm to about 180 cm and a suitable cross-sectional dimension for positioning within a subject's vasculature. The length of the shaft 110 can be a working length, such as a length that can be positioned within a subject's vasculature. In some embodiments, for example, the working length is about 70 cm to about 300 cm, about 150 cm to about 250 cm, or about 70 cm, about 80 cm, about 90 cm, about 100 cm, about 110 cm, about 120 cm, about 130 cm, about 140 cm, about 150 cm, about 160 cm, about 170 cm, about 180 cm, about 190 cm, about 200 cm, about 210 cm, about 220 cm, about 230 cm, about 240 cm, about 250 cm, about 260 cm, about 270 cm, about 280 cm, about 290 cm, or about 300 cm.

Referring now to FIGS. 2-5, the shaft of a delivery device can provide features that provide robust flexibility and reduce sliding friction.

Figure 2:
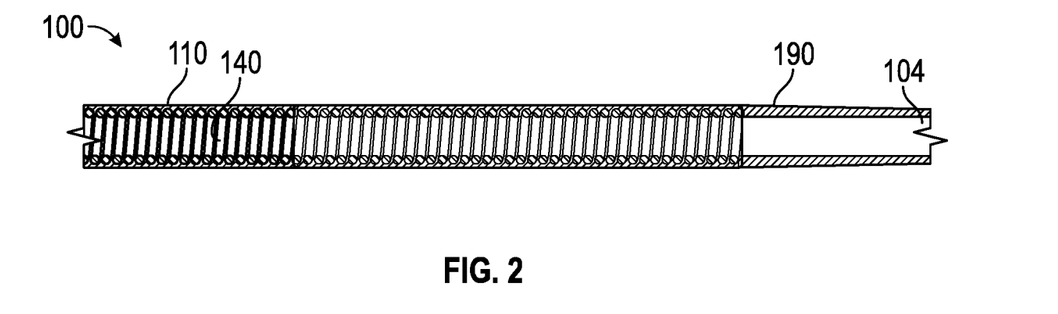
FIG. 2 illustrates a sectional view of a distal portion of a delivery device.

As shown in FIG. 2, the shaft 110 can be coupled to a distal tip 190. The distal tip 190 can define the distal end portion 104 of the delivery device 100. A lumen 140 can extend through both the shaft 110 and the distal tip 190. A distal portion of the distal tip 190 can extend beyond the shaft 110. The distal tip 190 can be radiopaque or include markers to provide visualization thereof during a procedure. Additionally or alternatively, other structures can be provided at, adjacent to, or between one or more of the shaft 110 and/or the distal tip 190 to facilitate visualization thereof.

The delivery device 100 can include the shaft 110 extending along a significant length thereof. For example, the shaft 110 can span a majority of the length of the entire delivery device 100. For example, the shaft 110 can span at least 50%, 60%, 70%, 80%, or 90% of the length of the entire delivery device 100. Along such a length, the delivery device 100 can optionally provide no structure other than the shaft 110. The shaft 110 can have a consistent and/or repeating pattern across its entire length. As such, the shaft 110 can define a significant portion of the overall delivery device 100, so that the features of the shaft 110 are provided across a significant length of the entire delivery device 100.

Figure 3:
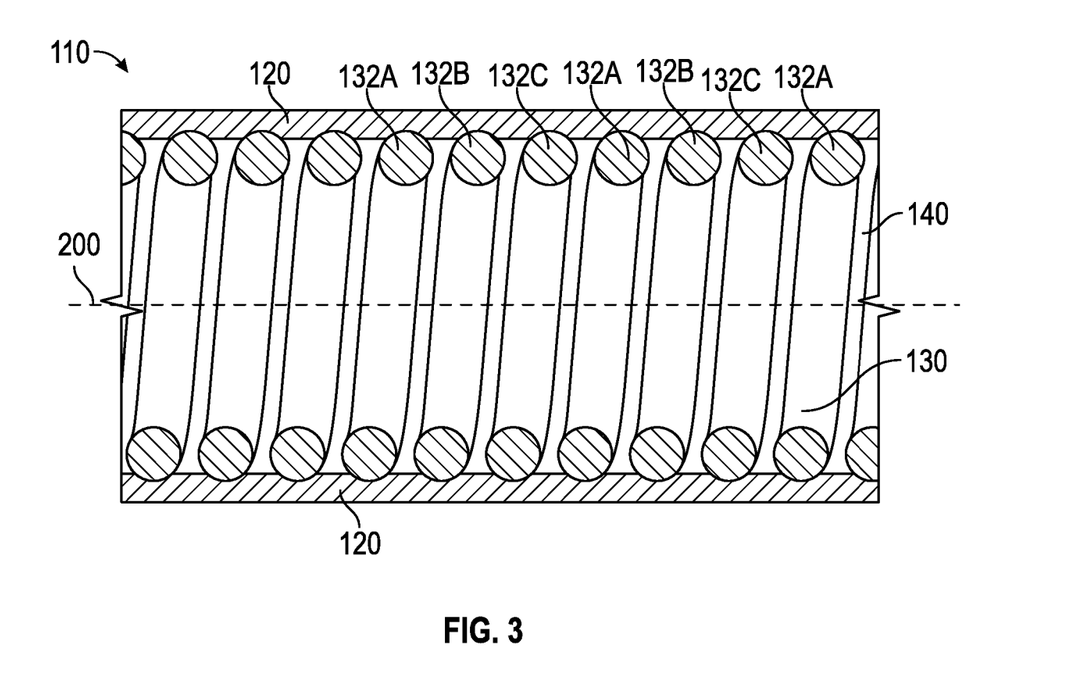
FIG. 3 illustrates a sectional view of a shaft of a delivery device.

As shown in FIG. 3, the shaft 110 can include a coil 130 formed by one or more filars 132 that extend helically along a length of the shaft 110. The winding pattern need not include an arrangement in which the filars 132 cross (e.g., braid) each other. Accordingly, each of the filars 132 can be arranged in a same chirality (i.e., right-handed or left-handed) as every other filar. As such, the shaft need not include a thickness formed by crossing (e.g., braided) filars 132. The filars 132 can be congruent with each other, such that they extend about the same axis 200 and differ by a translation along the axis 200. The filars 132 can have other properties in common, such as winding pitch angle, filar diameter, winding diameter, and the like. It will be understood that any two filars 132 can have different properties, such as winding pitch angle, filar diameter, winding diameter, and the like. It will be further understood that certain properties can be different across different filars 132 while maintaining consistent aggregate features. For example, different filars 132 can have different filar diameters yet provide a similar inner winding diameter so that the resulting lumen defined by the filars 132 is consistent across the multiple filars 132.

One or more filars 132 can be provided in a repeating pattern. For example, in FIG. 3, three filars 132A, 132B, and 132C are illustrated. It will be understood that any number of filars can be provided in a repeating pattern. For example, the shaft 110 can include 1, 2, 3, 4, 5, 6, 7, 8, 9, 10, or more than 10 filars that are wound together in a repeating pattern. Where only one filar 132 is included, the sole filar 132 defines the dimensions of the lumen 140 extending through the coil 130.

As further shown in FIG. 3, the shaft 110 can further include one or more jackets 120 that extends across multiple filars 132 of the coil 130 and/or multiple windings of the one or more filars 132. The jacket 120 can extend along a radially outer portion of the filar(s) 132 defined with respect to the axis 200 about which the filar(s) 132 are helically wound. The jacket 120 can include a material (e.g., polymer, polyurethane, polyimide, high-density polyethylene (HDPE), polytetrafluoroethylene, silicone, Pebex® (polyether block amide), and the like) and a shape that provides coverage about the filar(s) 132 of the coil 130 as well as flexibility to allow axially adjacent turns of the one or more filar(s) 132 to move toward and/or away from each other. The jacket 120 can be directly coupled to the filar(s) 132 of the coil 130 (e.g., reflowed thermoplastics or heat activated shrink-wrap).

For example, as shown in FIG. 3, portions of the jacket 120 can be coupled to radially outer portions of the filar(s) 132. Other portions of the jacket 120 can extend radially inwardly to fill spaces between axially adjacent turns of the one or more filars. The jacket 120 can extend only partially radially inward, such that the filar(s) 132, rather than the jacket 120, define the innermost boundary of the lumen 140. The jacket 120 can include a first material and an optional coating (e.g., PTFE, hydrophilic layer, etc.) thereon.

It will be understood that the jacket 120 can be secured to the coil 130 by fusion, and the like. For example, the jacket 120 can be fused to the coil 130 at regions of contact. The materials of each of the jacket 120 and the coil 130 (e.g., the outer layer thereof) can facilitate such fusion, for example, with compatible polymers. Additionally or alternatively, the jacket 120 can be loosely positioned over the coil 130 to allow the jacket and the coil 130 (or portions thereof) to slide, rotate, or otherwise move relative to each other.

The jacket 120 can define the outermost dimension of the shaft 110. The jacket 120 can be directly coupled to the filars 132 of the coil 130. The filars 132 can define the innermost dimension of the shaft 110 at the lumen 140. As such, the lumen 140 can be defined by the inner edges of the filars 132 of the coil 130, where such filars 132 are axially spaced apart from each other to form discontinuities along a pathway traversing the lumen 140.

The shaft 110 can consist of only the filars 132 (including coatings) of the coil 130 on a radially inner side of the shaft 110 and the jacket 120 (including coatings) on a radially outer side of the shaft 110. The delivery device 100 can consist of only the shaft 110 along a substantial length thereof (e.g., between a proximal end of the shaft 110 and a distal end of the shaft 110 connected to the distal tip 190). As such, optionally no other structures can be provided between the proximal end of the shaft 110 and a distal end of the shaft 110 (e.g., at the distal tip 190).

Figure 4:
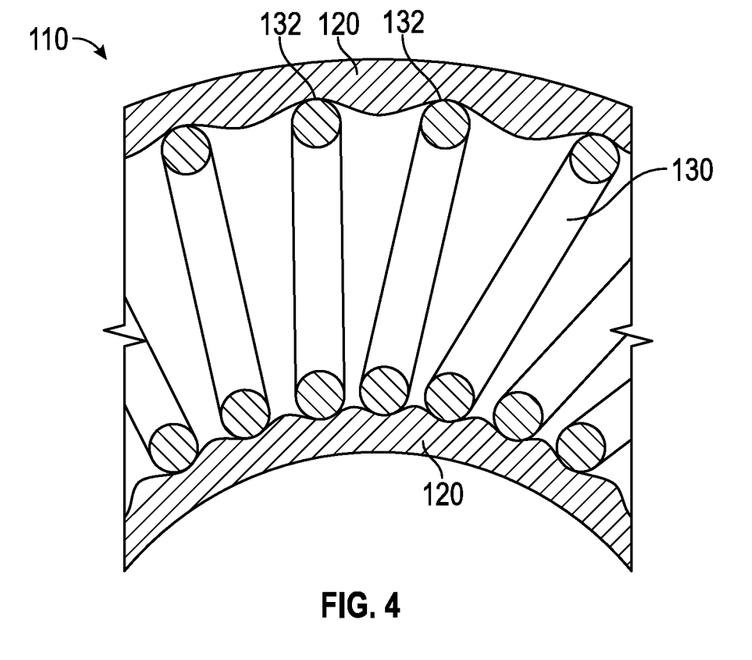
FIG. 4 illustrates another sectional view of a shaft of a delivery device.

As shown in FIG. 4, the jacket 120 can bend, stretch, and/or flex to allow the adjacent turns of the one or more filars 132 of the coil 130 to move toward and/or away from each other. Such flexibility allows the shaft 110 to bend while travelling through tortuous anatomy. It will be understood that such flexibility is multi-directional, such that the shaft 110 can deflect in any radial direction away from the central axis thereof. For example, the spacing between adjacent turns of the filars 132 can adjust to facilitate bending, stretching, and/or flexing of the shaft 110. Such flexibility can be enhanced by the omission of additional structure that would otherwise limit flexibility of the overall assembly.

Figure 5:
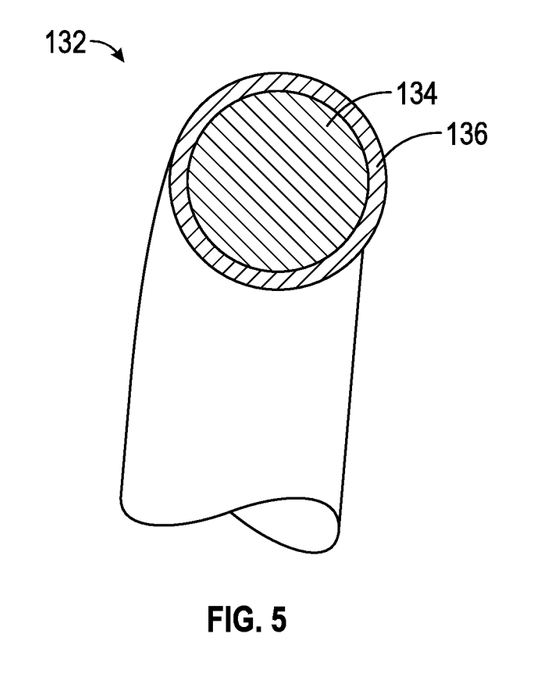
FIG. 5 illustrates a sectional view of a filar of a shaft of a delivery device.

Each of the filars 132 of the coil 130 can have a composition and assembly that provides the performance characteristics described herein. As shown in FIG. 5, any given filar 132 can include a core 134 and an outer layer 136.

The core 134 can provide structural support to hold a particular (e.g., helical) shape. For example, the core 134 can include a metal, such as a shape memory alloy (e.g., Nitinol). The core 134 can be shaped into a particular (e.g., helical) shape for assembly into the shaft. While the core 134 is shown as providing a circular (e.g., round) cross-sectional shape, the core 134 can have one or more other cross-sectional shapes (e.g., rectangular, square, polygonal, oval, and the like).

The core 134 can be shaped by one or more of a variety of techniques. For example, the core 134 can be formed initially as a wire and then heat set (e.g., annealed) into a particular (e.g., helical) shape. By further example, the core 134 can be shaped by annealing with resistive heating, hot working, cold working, milling, hammering, rolling, drawing, extruding, and/or combinations thereof. It will be understood that the core 134 can be held in or manipulated into the desired shape during such processes. As such, appropriate tools (e.g., mandrels, casts, molds, rollers, guides, etc.) can be employed to achieve the desired shape.

The outer layer 136 can be provided as a coating that covers an outer periphery of the core 134. As such, the outer layer 136 of the filars 132 can define the innermost dimension of the shaft at the lumen. The outer layer 136 can include a material (e.g., PTFE, hydrophilic layer, etc.) that provides low friction against devices passing through the lumen of the assembled shaft.

The outer layer 136 can be provided onto the outer surface of the core 134 by one or more of a variety of techniques. For example, the outer layer 136 can be deposited onto the core 134. By further example, the outer layer 136 can be deposited onto the core 134 by dipping, spraying, vapor deposition (e.g., physical vapor deposition and/or chemical vapor deposition), and/or combinations thereof.

It will be understood that the outer layer 136 can include one or more layers. For example, a primer coat (e.g., carbonaceous material) can be deposited onto the core 134 and a top coat (e.g., hydrophilic polymer) can be deposited onto the primer coat.

The outer layer 136 can be sufficiently thin such that the adjacent turns of the filars 132 do not touch one another and the filars 132 define a sufficiently wide lumen of the shaft while providing a small outer profile.

The one or more filars 132 can be arranged in the helical arrangement described herein and provided with the jacket 120 to define the shaft 110. The filars 132 can be prepared for assembly by performing the operations described herein in any one or a variety of sequences, with examples provided below. It will be understood that in each example, additional or fewer operations can be performed at any stage.

Assembly of the filars can include the operations of (in order): (1) shaping each filar (e.g., core) in its respective helical shape, (2) coating the entirety of each of the filars with an outer layer, and (3) combining multiple filars in a multi-filar helical winding arrangement Assembly of the filars can include the operations of (in order): (1) shaping each filar (e.g., core) in its respective helical shape, (2) combining multiple filars in a multi-filar helical winding arrangement, and (3) coating the entirety of each of the filars with an outer layer Assembly of the filars can include the operations of (in order): (1) coating the entirety of each of the filars (e.g., cores) with an outer layer, (2) shaping each filar in its respective helical shape, and (3) combining multiple filars in a multi-filar helical winding arrangement Assembly of the filars can include the operations of (in order): (1) coating the entirety of each of the filars (e.g., cores) with an outer layer, (2) combining multiple filars in a multi-filar helical winding arrangement, and (3) shaping each filar in its respective helical shape Assembly of the filars can include the operations of (in order): (1) combining multiple filars in a multi-filar helical winding arrangement, (2) shaping each filar in its respective helical shape, and (3) coating the entirety of each of the filars (e.g., cores) with an outer layer.

Assembly of the filars can include the operations of (in order): (1) combining multiple filars in a multi-filar helical winding arrangement, (2) coating the entirety of each of the filars (e.g., cores) with an outer layer, and (3) shaping each filar in its respective helical shape.

As described herein, the jacket 120 can define the radially outermost periphery of the shaft 110 along the length thereof, and the coil 130 can define the radially innermost periphery of the shaft 110 along the length thereof. Accordingly, the coil 130 (e.g., the outer layer 136 providing a lubricious coating) can define the lumen 140 extending through the shaft 110. No intervening structure need be provided between the jacket 120 and the coil 130. Accordingly, the jacket 120 can directly contact and engage the coil 130.

Figure 6:
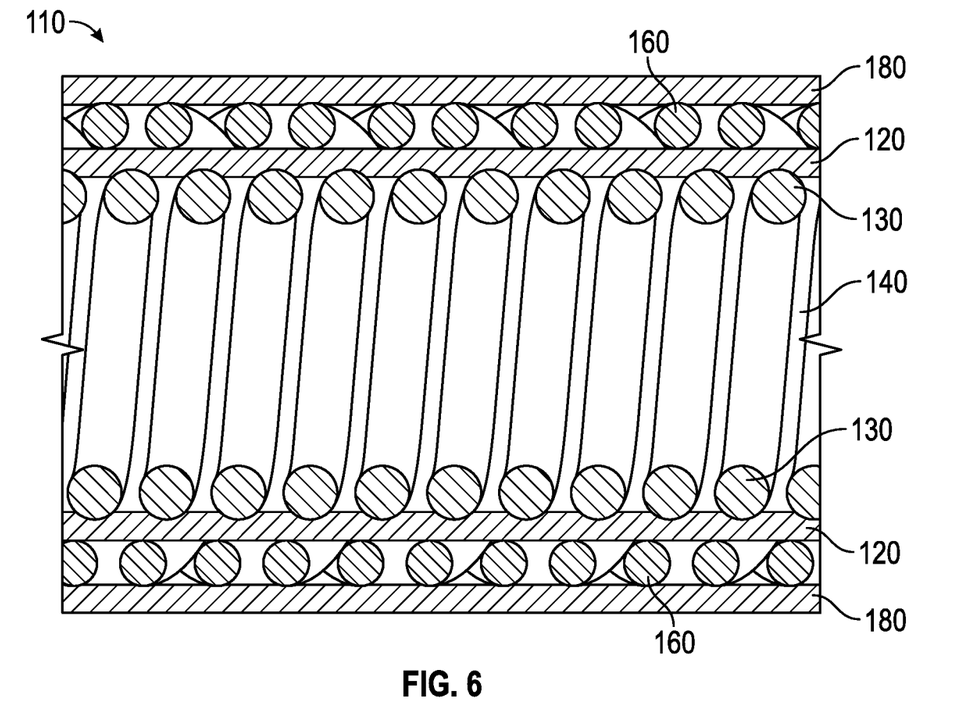
FIG. 6 illustrates a sectional view of a shaft of a delivery device.
Figure 7:
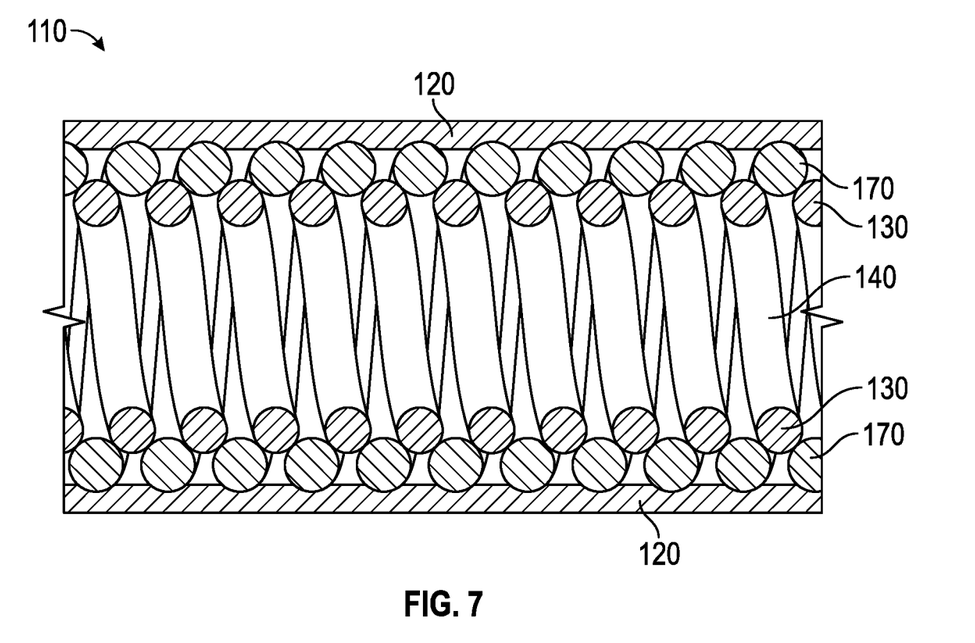
FIG. 7 illustrates a sectional view of a shaft of a delivery device.

Referring now to FIGS. 6 and 7, a shaft can include additional structure to provide support and desire mechanical characteristics, where applicable. For example, the shaft 110 can include one or more additional layers to add structural support. While the shaft 110 can include only a jacket and a coil, as described herein, additional layers can alternatively be added to modify structural characteristics and performance of the delivery device.

For example, as shown in FIG. 6, the shaft 110 can include a support layer 160 extending about the jacket 120. The support layer 160 can include an arrangement of a braid and/or a coil that provide mechanical support (e.g., column strength, etc.). The support layer 160 can surround the jacket 120 and/or be coupled thereto.

The support layer 160 can include one or more braided wires. The wire, or segments thereof, can cross each other at multiple locations according to a weave pattern. Additionally or alternatively, the support layer 160 can include a coil formed by one or more helically wound wires. The chirality (i.e., right-handed or left-handed) of the coil in the support layer 160 can be the same or opposite with respect to the coil 130. For example, where the coil 130 has a winding direction (e.g., chirality), the coil in the support layer 160 can have an opposite chirality, such that torque applied in either of two directions can be in the same direction as one of the coils.

It will be understood that any number of layers can be provided with or as part of the support layer 160. Such layers can be the same or different than each other. For example, multiple layers within the support layer 160 can each include a coil, where the coils have the same or different winding directions (e.g., chirality).

As further shown in FIG. 6, an outer jacket 180 can be provided about the support layer. The outer jacket 180 can define the radially outermost periphery of the shaft 110 along the length thereof. The outer jacket 180 can include a material (e.g., polymer, polyurethane, polyimide, high-density polyethylene (HDPE), polytetrafluoroethylene, silicone, Pebex® (polyether block amide), and the like). The outer jacket 180 can include an optional coating (e.g., PTFE, hydrophilic layer, etc.) thereon.

As shown in FIG. 7, the shaft 110 can include an intermediate layer 170 extending about the jacket 120. The intermediate layer 170 can include an arrangement of a coil and/or a braid that provide mechanical support (e.g., column strength, etc.). The intermediate layer 170 can be positioned radially between the jacket 120 and the coil 130.

The intermediate layer 170 can include a coil formed by one or more helically wound wires. The chirality (i.e., right-handed or left-handed) of the coil in the intermediate layer 170 can be the same or opposite with respect to the coil 130. For example, where the coil 130 has a winding direction (e.g., chirality), the coil in the intermediate layer 170 can have an opposite chirality, such that torque applied in either of two directions can be in the same direction as one of the coils. Additionally or alternatively, the intermediate layer 170 can include one or more braided wires. The wire, or segments thereof, can cross each other at multiple locations according to a weave pattern.

It will be understood that any number of layers can be provided with or as part of the intermediate layer 170. Such layers can be the same or different than each other. For example, multiple layers within the intermediate layer 170 can each include a coil, where the coils have the same or different winding directions (e.g., chirality).

Figure 8:
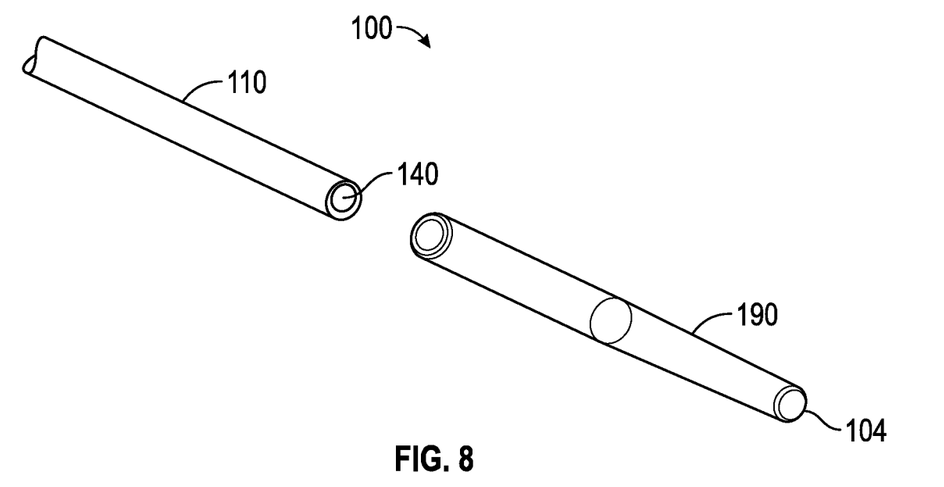
FIG. 8 illustrates a perspective exploded view of a distal portion of a delivery device.
Figure 9:
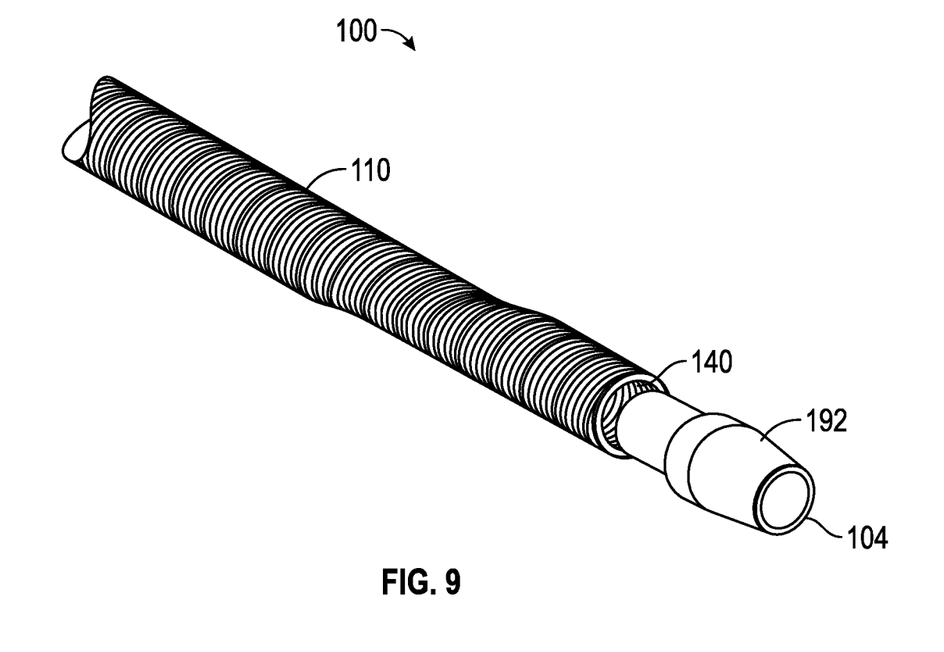
FIG. 9 illustrates a perspective exploded view of a distal portion of a delivery device.

Referring now to FIGS. 8 and 9, the delivery device can include a distal tip defining a distal end portion of the delivery device. The distal tip can provide a continuation of the lumen extending through the shaft and terminate in an opening for the lumen.

As shown in FIG. 8, the distal tip 190 can extend over and about at least a portion of the shaft 110, such that a distal portion of the shaft 110 resides within a portion of the distal tip 190. The distal portion of the distal tip 190 can be tapered and/or provide an atraumatic shape. The distal tip 190 can be a flexible material (e.g., polymer) having a length that allows it to bend for navigating tortuous anatomy. The distal tip 190 can be coupled to the coil and/or the jacket of the shaft 110. For example, a polymer material of the distal tip 190 can be heat treated to melt onto and/or with the coil and/or the jacket of the shaft 110.

As shown in FIG. 9, the shaft 110 can extend over and about at least a portion of the distal tip 190, such that a proximal portion of the distal tip 190 resides within a portion of the shaft 110. The distal tip 190 can be a rigid material (e.g., metal) for applying a force to a target (e.g., CTO). The distal tip 190 can have a sufficiently short length that allows it to navigate tortuous anatomy despite its rigidity.

Accordingly, the embodiments described herein provide a delivery device that has a low outer profile and high flexibility for navigating tortuous anatomy. An inner lumen thereof provides adequate space for delivery devices to target anatomy. Additionally, the delivery device maintains the patency of its lumen even when positioned within tortuous anatomy. The turns of the filar(s) of the shaft adjust their axial spacing relative to each other to avoiding buckling that would otherwise result in a narrowing of the inner lumen.

The delivery device 100 described herein can be used to position an interventional device. An example of such an interventional device is the crossing device disclosed in International Patent Application No. PCT/US2010/047170, filed Aug. 30, 2010, entitled "SYSTEMS, METHODS AND DEVICES FOR ABLATION, CROSSING, AND CUTTING OF OCCLUSIONS," which is incorporated herein by reference in its entirety. For example, an interventional device can be positioned with the delivery device 100 and actuated (e.g., advanced, retracted, rotated, etc.) and provide features (e.g., blades, edges, cutting implements, etc.) that facilitate penetration or other actions with respect to the target anatomy (e.g., CTO, vessel wall, etc.).

The delivery device 100 described herein can be used to position a therapeutic or implantable device. An example of such a device is the expandable device disclosed in U.S. Patent Publication No. 2017/100266, filed Mar. 27, 2017, entitled "Stents having protruding drug-delivery features and associated systems and methods," which is incorporated herein by reference in its entirety. For example, an expandable device can be positioned with the delivery device 100 and expanded when positioned at the target anatomy (e.g., vessel wall, etc.).

Vessels in which the delivery devices described herein may be sized and shaped for placement include arteries, such as coronary arteries, peripheral arteries, carotid arteries, circle of willis, anterior cerebral artery, middle cerebral artery, posterior cerebral artery, any of the lenticulostriate arteries, renal arteries, femoral arteries, veins, such as cerebral veins, saphenous veins, arteriovenous fistulas, or any other vessel that may contain a treatment site. Other vessels are likewise contemplated, and the delivery devices can be formed and/or selected according to a known destination and/or travel pathway within the body of a patient.

Various examples of aspects of the disclosure are described below as clauses for convenience. These are provided as examples, and do not limit the subject technology.

Clause A: a delivery device comprising: a proximal end; a distal tip; and a shaft defining a lumen and extending between the proximal end and the distal tip, the shaft comprising: a coil comprising a filar extending helically about an axis to define the lumen, the filar comprising a metal core and a polymer outer layer coating the metal core; and a jacket extending about the coil.

Clause B: a delivery device comprising: a proximal end portion; a distal end portion; and a shaft defining a lumen and extending between the proximal end portion and the distal end portion, the shaft comprising: a coil comprising a lubricious material defining a surface of the coil, the lubricious material defining a radially innermost portion extending along an entirety of the shaft; and a jacket extending about the coil.

Clause C: a method of assembling a shaft for a delivery device, the method comprising: coating a core of a filar with an outer layer; shaping the filar in a helical shape to form a coil winding about a lumen; and covering the coil with a jacket extending longitudinally across the coil, wherein the outer layer of the coil forms a radially innermost portion of the delivery device at the lumen.

One or more of the above clauses can include one or more of the features described below. It is noted that any of the following clauses may be combined in any combination with each other, and placed into a respective independent clause, e.g., clause A, B, or C.

Clause 1: the filar is one of multiple filars extending helically about the axis to form the coil.

Clause 2: the jacket defines a radially outermost portion of the shaft.

Clause 3: the outer layer of the coil defines a radially innermost portion of the shaft.

Clause 4: the jacket extends partially radially inwardly between adjacent windings of the coil.

Clause 5: the distal tip extends within a distal portion of the shaft.

Clause 6: the distal tip extends about a distal portion of the shaft.

Clause 7: a support layer extending about the jacket, the support layer forming a coil or a braid.

Clause 8: an intermediate element radially between the coil and the jacket, the intermediate element forming a coil or a braid.

Clause 9: the coil comprises multiple filars extending helically about an axis.

Clause 10: the coil further comprises a core supporting the lubricious material coated on the core.

Clause 11: the jacket defines a radially outermost portion of the shaft.

Clause 12: the shaft defines over 50% of a total length of the delivery device.

Clause 13: combining the filars in a multi-filar helical winding arrangement to form the coil.

Clause 14: shaping the filar comprises cold working the core into the helical shape while the outer layer is coated on the core.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

Generally, unless the context indicates otherwise, the terms "distal" and "proximal" within this disclosure reference a position relative to an operator or an operator's control device. For example, "proximal" can refer to a position closer to an operator or an operator's control device, and "distal" can refer to a position that is more distant from an operator or an operator's control device.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

The invention claimed is:

1. A delivery device comprising:
   a proximal end;
   a distal tip; and
   a shaft defining a lumen and extending between the proximal end and the distal tip, the shaft comprising:
      a coil comprising a filar extending helically about an axis to define the lumen, the filar comprising a metal core and a polymer outer layer coating the metal core; and
      a jacket extending about the coil, wherein the jacket extends partially radially inwardly between adjacent windings of the coil, wherein the jacket is positioned over the coil to allow the jacket and the coil to slide relative to each other.

2. The delivery device of claim 1, wherein the filar is one of multiple filars extending helically about the axis to form the coil.

3. The delivery device of claim 1, wherein the jacket defines a radially outermost portion of the shaft.

4. The delivery device of claim 1, wherein the outer layer of the coil defines a radially innermost portion of the shaft.

5. The delivery device of claim 1, wherein the jacket extends partially radially inwardly between adjacent windings of the coil.

6. The delivery device of claim 1, wherein the distal tip extends within a distal portion of the shaft.

7. The delivery device of claim 1, wherein the distal tip extends about a distal portion of the shaft.

8. The delivery device of claim 1, further comprising a support layer extending about the jacket, the support layer forming a coil or a braid.

9. The delivery device of claim 1, further comprising an intermediate element radially between the coil and the jacket, the intermediate element forming a coil or a braid.

10. A delivery device comprising:
    a proximal end portion;
    a distal end portion; and
    a shaft defining a lumen and extending between the proximal end portion and the distal end portion, the shaft comprising:
       a coil comprising a core and polytetrafluoroethylene defining a surface of the coil, the polytetrafluoroethylene defining a radially innermost portion extending along an entirety of the shaft; and
       a jacket comprising a thermoplastic extending about and engaging the coil, wherein the jacket is wrapped onto the coil to allow the jacket and the coil to move relative to each other.

11. The delivery device of claim 10, wherein the coil comprises multiple filars extending helically about an axis.

12. The delivery device of claim 10, wherein the jacket defines a radially outermost portion of the shaft.

13. The delivery device of claim 10, wherein the shaft defines over 50% of a total length of the delivery device.

14. The delivery device of claim 10, further comprising a support layer extending about the jacket, the support layer forming a coil or a braid.

15. The delivery device of claim 10, further comprising an intermediate element radially between the coil and the jacket, the intermediate element forming a coil or a braid.

16. A delivery device comprising:
    a proximal end;
    a distal tip; and
    a shaft defining a lumen and extending between the proximal end and the distal tip, the shaft comprising:
       a coil comprising a filar extending helically about an axis to define the lumen, the filar comprising a metal core and a polymer outer layer coating the metal core;
       a first jacket engaging the coil along a length of the coil;
       a support layer engaging the first jacket along a length of the first jacket, the support layer forming a coil or a braid; and
       a second jacket engaging to the support layer along a length of the support layer.

17. The delivery device of claim 16, wherein the first jacket is wrapped onto the coil to allow the first jacket and the coil to move relative to each other.

18. The delivery device of claim 16, wherein the polymer comprises polytetrafluoroethylene.

* * * * *